United States Patent [19]  [11] Patent Number: 4,915,693
Hessel  [45] Date of Patent: Apr. 10, 1990

[54] PRESSURIZED FLUID DISPENSER

[75] Inventor: Stephen R. Hessel, Poway, Calif.

[73] Assignee: Baxter International, Inc., Deerfield, Ill.

[21] Appl. No.: 240,757

[22] Filed: Sep. 2, 1988

Related U.S. Application Data

[63] Continuation of Ser. No. 935,021, Nov. 26, 1986, Pat. No. 4,769,008.

[51] Int. Cl.[4] ............................................. A61M 37/00
[52] U.S. Cl. .............................. 604/132; 128/DIG. 12
[58] Field of Search .................................. 604/74–76, 604/132, 133; 128/DIG. 12; 222/94, 95, 211, 105, 212, 215

[56]  References Cited

U.S. PATENT DOCUMENTS

| | | | |
|---|---|---|---|
| 3,361,303 | 1/1968 | Jacuzzi | 222/183 |
| 3,412,906 | 11/1968 | Dinger | 222/183 |
| 3,468,308 | 9/1969 | Bierman | 128/214 |
| 3,469,578 | 9/1969 | Bierman | 128/214 |
| 3,506,005 | 4/1970 | Gilio et al. | 128/214 |
| 3,672,543 | 6/1972 | Roper et al. | 222/183 |
| 3,677,444 | 8/1972 | Merrill | 222/135 |
| 3,698,595 | 10/1972 | Gortz et al. | 220/63 R |
| 3,738,538 | 6/1973 | Roper et al. | 222/183 |
| 3,791,557 | 2/1974 | Venus, Jr. | 222/105 |
| 3,796,356 | 3/1974 | Venus, Jr. | 222/212 |
| 3,876,115 | 4/1975 | Venus, Jr. et al. | 222/183 |
| 3,961,725 | 6/1976 | Clark | 222/1 |
| 3,981,415 | 9/1976 | Fowler et al. | 222/95 |
| 4,318,400 | 3/1982 | Peery et al. | 128/214 F |
| 4,386,929 | 6/1983 | Peery et al. | 604/132 |
| 4,419,096 | 12/1983 | Leeper et al. | 604/132 |

Primary Examiner—Jerome L. Kruter
Attorney, Agent, or Firm—Knobbe, Martens, Olson & Bear

[57]  ABSTRACT

Disclosed is an elastomeric bladder infusion pump which may be used for delivering a pharmaceutically active material to a patient at a substantially constant flow rate. A unitary internal stress member or mandrel is disposed within the bladder, prestressing the bladder in both the axial and radial dimensions.

5 Claims, 2 Drawing Sheets

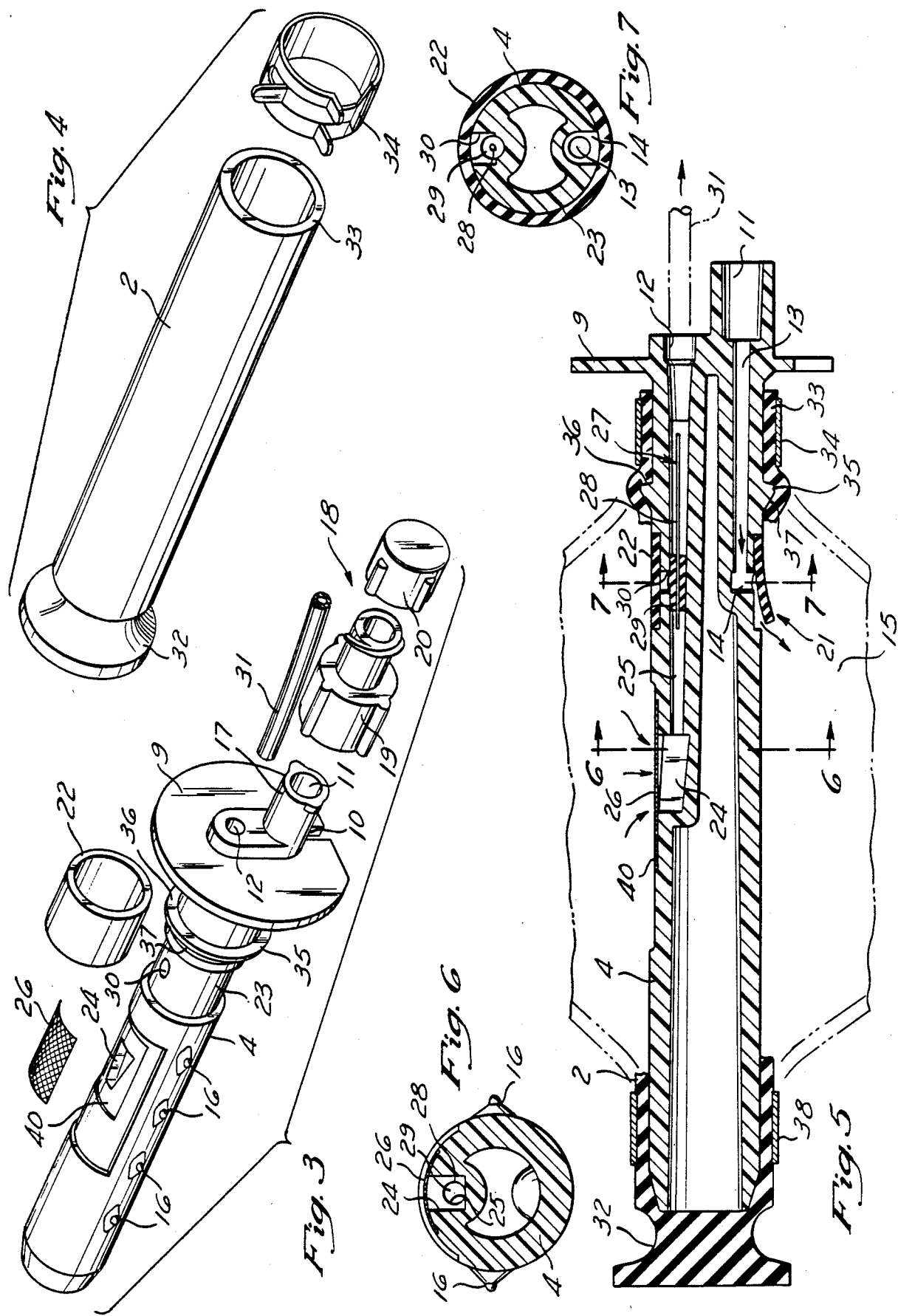

PRESSURIZED FLUID DISPENSER

This application is a continuation of application Ser. No. 935,021, filed 11/26/86 now U.S. Pat. No. 4,769,008.

BACKGROUND OF THE INVENTION

The present invention relates to a compact elastomeric bladder infusion pump for administering a pharmaceutically active material at a substantially constant flow rate over the service cycle of the pump. More particularly, the present invention relates to an improved infusion pump having an internal stress member disposed within the bladder, which prestresses the bladder in both the axial and radial directions thereby enabling the bladder to exert a substantially constant pressure on the contents thereof throughout the service cycle. Although a variety of elastomeric bladder infusion pumps are known, there remains a need for an infusion pump which is simple and inexpensive from a manufacturing standpoint, yet is capable of delivering its contents at a substantially constant rate.

None of the prior art elastomeric bladder infusion pumps known to the inventor may be easily manufactured, at a low per-unit cost, yet exhibit a high degree of reliability in terms of storage life and the ability to deliver substantially all of the contents at a substantially constant flow rate.

SUMMARY OF THE INVENTION

The present invention provides an elastomeric bladder infusion pump. A significant feature of this invention is that the pump constructed in accordance with the invention delivers substantially all of the pharmaceutically active material contained therein at a substantially constant flow rate while being inexpensive, reliable and simple to manufacture.

In accordance with one aspect of the present invention, a portable infusion pump for delivering a quantity of pharmaceutically active material at a substantially constant flow rate has been provided. The infusion pump comprises an elastomeric bladder having at least one open end, and an elongate stress member extending concentrically within the entire length of the hollow portion of the bladder and having a fluid tight seal therewith. Both a filling port and an exit port are provided on the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. Preferably, the axial stress imparted by the internal stress member is from about 35 to 60 percent, and the radial stress is preferably from about 15 to about 40 percent, measured as a percent increase in the specified dimension caused by the internal stress member, compared to that dimension on a completely relaxed bladder.

An important feature of the infusion pump of the present invention is the provision of a one-way valve on the stress member, which permits flow in the influent lumen only in the direction of the interior of the bladder. This one way valve is a substantial advantage over the prior art in that it permits filling of the pump by any pressurized means having a luer connection thereon. Contrariwise, the prior art infusion pumps generally require piercing of a septum during the filling procedure.

In the preferred embodiment, a controlling means for regulating the effluent flow comprising a capillary tube of known internal diameter, is concentrically disposed within the effluent lumen through said internal stress member.

An additional feature of the invention is that the internal stress member is advantageously provided with a very simple, yet very effective visual display when the bladder has been emptied a predetermined amount. As described hereinafter, a plurality of indicator bumps, spaced apart, and extending in a radially outward direction provide a visual indication that the bladder is nearing the end of its duty cycle.

In one embodiment of the present invention, a stainless steel filter is disposed upstream of the exit port, on the exterior of the internal stress member traversing the transverse effluent duct through which the interior of the bladder is in fluid communication with the effluent lumen.

Further objects, features and advantages of the present invention will become apparent from the detailed description of preferred embodiments which follows, when considered together with the attached figures.

BRIEF DESCRIPTION OF THE DRAWINGS

FIG. 3 is an exploded perspective view of the internal stress member of the present invention.

FIG. 4 is a perspective view of one embodiment of the bladder of the present invention, in its uninflated state.

FIG. 5 is a partial, cross-sectional view of a preferred embodiment of the present invention. In this view, a portion of the bladder is shown in phantom.

FIG. 6 is a partially sectional view taken along the line 6—6 of FIG. 5, with some features omitted for clarity.

FIG. 7 is a partially sectional view taken along the line 7—7 of FIG. 5, with some features omitted for clarity.

DETAILED DESCRIPTION OF PREFERRED EMBODIMENTS

Figure 1:
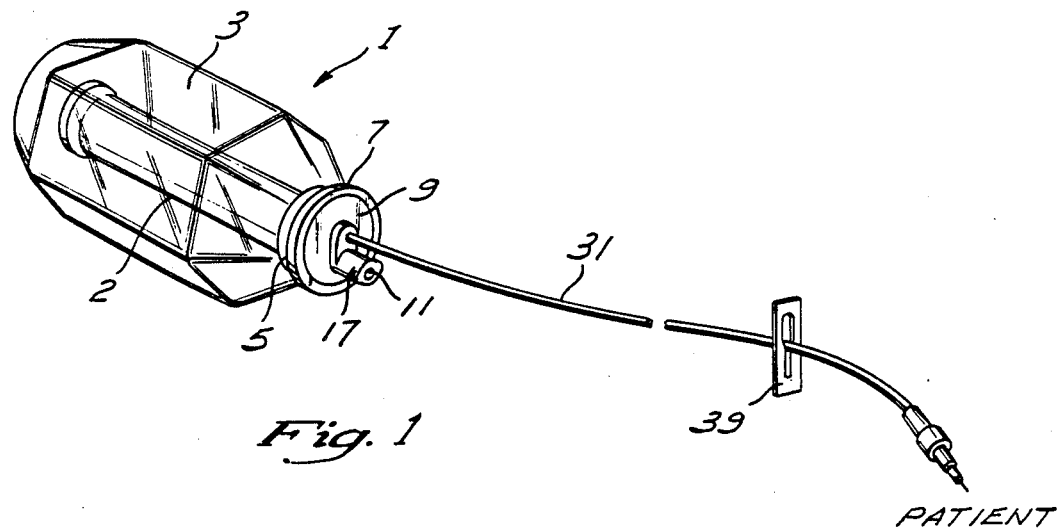
FIG. 1 is a perspective view of one embodiment of the infusion pump of the present invention.
Figure 2:
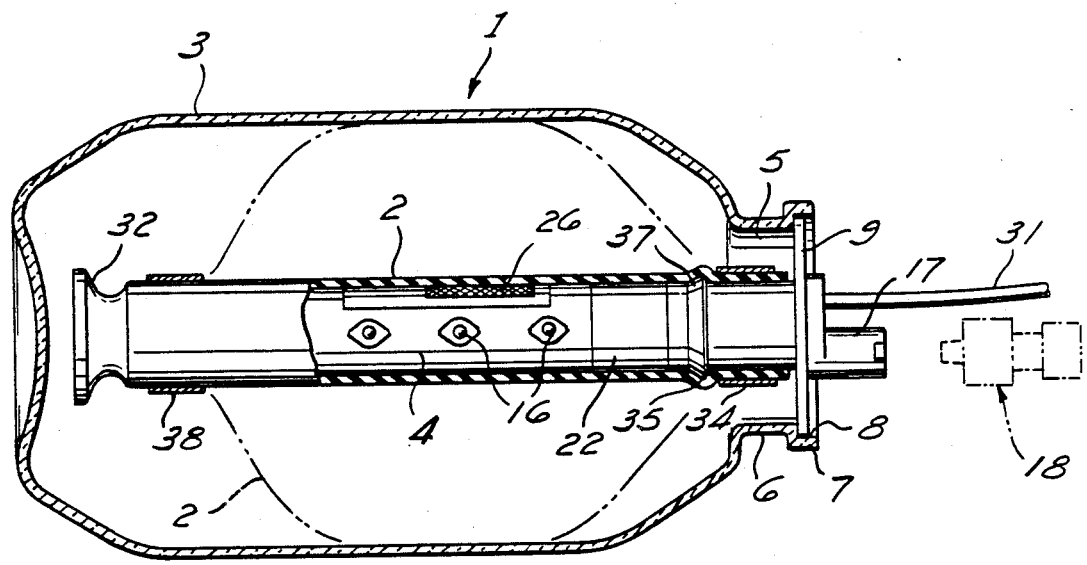
FIG. 2 is an elevational partial sectional view of the infusion pump of the present invention.

Referring to FIGS. 1 and 2, there is provided in accordance with one aspect of the present invention, a constant pressure infusion pump 1 comprising an elastomeric collapsing bladder 2 disposed within a generally tubular outer casing 3 and concentrically about an internal stress member 4. The cross-sectional dimension of tubular casing 3 is selected so that it limits the radial outward expansion of bladder 2, thereby preventing rupture due to overstressing of the bladder by filling. The expanded state configuration of a preferred embodiment of the present invention is illustrated in phantom in FIG. 2. The bladder 2 may comprise any of a variety of elastomeric compositions well known in the art, which will be substantially inert in the presence of the pharmaceutically active material contained in the interior 8 thereof. By inert, it is meant that the material will not adversely react with or dissolve in the pharmaceutically active contents of the filled bladder, nor will it catalyze or initiate any deleterious reactions of that material.

For example, suitable vulcanized synthetic polyisoprenes are known in the prior art. Natural latex or silicone rubber having high resilience capabilities may also be used. Most preferably, the bladder comprises a blend of natural and synthetic rubbers, having a high elasticity and low hysteresis. In any case, the bladder material is selected (i) to exert sufficient force on the fluid so as to expel substantially all of the contents of the bladder after having been filled and in storage, typically for some seven days or more, and (ii) such that the infusion pump can be stored in the assembled (stressed) but not filled state for as much as a year or longer, without affecting the bladder's capability to expel its contents at a substantially constant rate.

The casing 3 is advantageously formed from any of a variety of known thermal distortion moldable polymeric materials such as acrylic or styrene, which will protect the material of the bladder from ultraviolet light initiated degradation, yet are substantially transparent to visible light thereby permitting visual observation of the components of the infusion pump. Casing 3 is provided with an opening 5 at the proximal end thereof, for receiving said internal stress member 4. Opening 5 has a neck 6 of lesser internal diameter than that of the axially directed annular flange 7, thereby forming an annular seating ring 8 for receiving a mounting disc 9 disposed near the proximate end of stress member 4. The disc 9 is provided with at least one perforation 10 therethrough, and may be mounted against the seating ring 8 using known clamps, adhesives, or a friction snap fit.

A generally cylindrical internal stress member 4 comprises both a filling port 11 and an exit port 12 at the proximal end thereof, best illustrated in FIG. 5. Filling port 11, by way of lumen 13, and transverse influent duct 14, is in fluid communication with the interior 15 of the bladder 2. The stress member 4 may be produced in accordance with known thermoplastic forming techniques, and preferably comprises acrylic, styrene or any other rigid thermoplastic material that is substantially inert in the environment of the intended pharmaceutically active material. If it becomes desirable from a manufacturing standpoint, the stress member 4 may be formed from other materials and thereafter be provided with a continuous coating of an appropriate inert substance. Geometrically, the stress member 4 preferably has a substantially uniform, circular cross-section throughout that portion of its axial length disposed within the interior 15 of bladder 2, interrupted only by a plurality of indicator bumps 16, detailed infra.

Preferably, filling port 11 is provided with a male luer attachment 17 for connection to a filling apparatus. A double luer cap 18 is provided, which has a first female luer cap 19 for engagement with the male luer 17 on said filling port 11, and a second female luer cap 20 attached to said first luer cap 19. When luer cap 19 is removed for filling the bladder 2, the second luer cap 20 remains aseptic and may be detached from luer cap 19 for sealing filling port 11. Alternatively, luer 17 may be aseptically sealed with a sealing membrane instead of the double luer cap 18. The membrane may be removed at the time of filling, and, after filling, the filling port 11 may be sealed with a sterile standard size luer cap.

Backflow out of the transverse influent duct 14 of the material under pressure within the interior 15 of bladder 2 is prevented by one-way valve 21, comprising an elastic valve band 22 disposed coaxially about internal stress member 4 and in overlapping engagement with transverse influent duct 14. As illustrated in FIG. 3, the internal stress member 4 is provided with an annular recess 23 for receiving valve band 22 so that the outside diameter of valve band 22 is substantially the same as the diameter of the adjacent portions of the stress member 4. Thus, the generally cylindrical configuration of the stress member 4 with the valve band 22 in place is maintained, thereby permitting the deflated bladder 2 to snugly fit against stress member 4 minimizing spaces for trapped air in the infusion pump.

Pressure from an influent stream through transverse influent duct 14 will cause momentary displacement of elastic valve band 22, as illustrated in FIG. 5. As a result, the influent stream is permitted to pass into the interior 15 of bladder 2. Upon termination of the influent stream, valve band 22 will elastically return to sealingly obstruct duct 14, thereby preventing leakage of material from the interior 15 of bladder 2 back out through the transverse influent duct 14.

The interior 15 of bladder 2 is in fluid communication through transverse effluent duct 24 with efflulent lumen 25 and exit port 12, disposed on the proximal end of stress member 4. In a preferred embodiment of the present invention, the lumen 25 extends in a distal direction through the stress member 4 at least far enough that effluent duct 24 is located near the center of the inflated bladder. Thus, in an embodiment wherein the inflated bladder 2 is approximately spherical, the effluent duct 24 is disposed approximately midway along stress member 4 between the proximal and distal points at which the axial end regions of the bladder 2 are in sealing engagement with the stress member 4. Positioning effluent duct 24 away from the axial ends and near the midpoint of the interior space 15 of the bladder 2 reduces the likelihood that any air bubbles in bladder 2 will enter lumen 25 and be introduced into the patient.

Thus, the unitary stress member 4 has a first influent lumen 13 and a second effluent lumen 25 extending therethrough for introduction and removal, respectively, of material from the interior 15 of bladder 2. These lumen preferably are substantially parallel to each other, and each is provided with a port at the proximal end of the stress member 4.

Stress member 4 may further be provided with a screen or mesh 26 traversing effluent duct 24 and held in place by an adhesive, to preclude introduction into the patient of any pharmaceutical material that may have become crystallized during storage, or any other solid matter. Screen 26 may comprise stainless steel, platinum wire or other suitable metal, or any of a variety of polymers such as polytetrafluoroethylene, having a porous or multifilament configuration capable of operating as a screen, and which will be substantially unreactive in the presence of the pharmaceutical material. The mesh size should be selected so that the sum of the flow paths through the mesh will permit sufficient flow that the mesh will not be a factor in the overall flow rate of the infusion pump. Placement of screen 26 may be anywhere near or downstream from duct 24, the illustrated preferred embodiment having been selected for ease of manufacture. The stress member 4 may be provided with a shallow depression 40 for receiving screen 26.

Effluent lumen 25 is further provided with a flow rate regulator 27, which may comprise capillary tube 28 having a lumen therethrough of known cross-section and length, disposed coaxially within effluent lumen 25.

The regulator 27 regulates in a controlled manner the effluent stream against pressure developed from the bladder 2. Any of a variety of commercially available capillary tubes may be advantageously employed, such as glass capillary tubes or hypodermic needle stock. In order to accurately determine the flow rate of a given capillary tube, the precise internal radius of that tube is first determined. While the manufacturer's specifications are accurate enough for most capillary tube applications small machining tolerances become important for the purpose of the present invention due to the known relationship that flow rate is proportional to the fourth power of the internal radius of a tube. The true radius of, for example, hypodermic needle stock having a specified I.D. of approximately 0.004 inch, is advantageously determined by first measuring the pressure drop through a tube of known length in dynes/cm$^2$. A gas maiantained at a known pressure is directed through the capillary, and the pressure drop and flow rate empirically determined with the capillary discharging into normal atmospheric pressure. Having determined the flow rate, the pressure drop, as well as the length of the capillary tube, the internal radius of the capillary tube can be determined from Poiseuille's Law, as expressed in the equation:

$$Q = (Pr^4)/8Ln$$

where Q is the flow rate in cc/sec through the capillary tube, P is the pressure drop through the tube in dynes/cm$^2$, r is the internal radius of the tube in cm, L is the length of the tube in cm, and n is the viscosity in poise. Solving the equation provides the true internal radius of a given piece of capillary stock. Once the true internal radius is known, any desired flow rate can be inserted into the equation, from which the length of a piece of that capillary tube necessary to permit the desired flow rate can be calculated. Thus, standard hypodermic needle stock can be appropriately cut to length to provide precise predetermined delivery rates such as anywhere from about 50 ml/hr or less to about 500 ml/hr or greater, including 100 ml/hr, 200 ml/hr, or any other desired rate.

The capillary tube 28 is advantageously secured within effluent lumen 25 by an adhesive material 29, as shown in FIG. 5, or a preformed member (not shown). Material 29 provides sealing engagement between the walls defining effluent lumen 25 and the regulator 27 to avoid any fluid communication around the outside of the capillary tube.

The stress member 4 is advantageously provided with a glue port 30 which allows exposure of a capillary tube 28 extending through effluent lumen 25 to the exterior for receiving a quantity of the adhesive 29 such as urethane based UV cured epoxy or other material that will be chemically inert in the presence of a pharmaceutically active material contained within the interior 15 of bladder 2 and will block any fluid communication through glue port 30.

Pharmaceutically active material contained within the interior 15 of bladder 2 is directed from regulating means 27 to the patient (not illustrated) by means of conventional I.V. tubing 31 sealingly attached to exit port 12.

Referring to FIG. 4, there is illustrated a preferred embodiment of the bladder 2 of the present invention, not intended as a scale representation, comprising an elastic generally cylindrical member for defining a space which, in the unexpanded state, is of known interior cross-sectional and axial dimensions. The bladder 2 may be closed at the distal end 32 as shown. Alternatively, as described below, the bladder may be formed with an open distal end 32. The bladder 2 is open at the proximal, or discharge end 33, the latter end being coaxially disposed about and in sealing engagement with internal stress member 4, as illustrated in FIG. 2. This seal is accomplished or enhanced by means of an annular clamp 34 extending therearound.

Distal to clamp 34 on internal stress member 4 is an annular flange or shoulder 35 which, in cooperation with clamp 34, prevents migration of the discharge end of bladder 2 in a distal direction due to elastic forces generated by the filled bladder, which will be detailed infra. Annular flange 35 comprises a proximal surface 36 and a distal surface 37, which extend radially outwardly from said stress member 4 and converge to form a relatively sharp angle at the radially outward most portion of annular flange 35. As illustrated in FIG. 5, the distal surface 37 is inclined outwardly from the surface of stress member 4 at a more gradual angle than surface 36, thereby enhancing the securing function of annular flange 35. A similar result may be achieved, without the use of annular flange 35, by providing stress member 4 with an annular depression (not illustrated) for receiving a clamp 34, an O-ring, or other conventional sealing means. The seal may alternatively be effected using any of a variety of known adhesives, such as an epoxy. In the embodiment illustrated in FIG. 5, the size of the annular flange 35 generally is minimized so that it is not a factor in the deflation characteristics of the bladder.

At the distal end of the bladder 2, there may be provided a second clamp 38, illustrated as an annular band, for clamping the distal end 32 of bladder 2 to the distal end of internal stress member 4 in sealing engagement. Use of this clamp will substantially eliminate any axial component of expansion of the bladder. Although the bladder 2 is illustrated in FIG. 4 as having been molded with a closed end at the distal end 32 thereof, use of clamp 38 also enables the use of bladders which have been extruded with an opening at each end and a central lumen extending therethrough.

The unexpanded length of bladder 2 is less than the axial length of that portion of stress member 4 disposed therein. Likewise, the expanded interior cross sectional area of bladder 2 is less than the cross sectional are of the portion of stress member 4 disposed therein. Thus, the bladder 2 is both axially and radially prestressed when concentrically disposed about stress member 4. It has been determined that prestress that is less than the prestress disclosed in the prior art optimizes the advantages of the present invention. Preferably, the axial prestress will be in the range of from about 35% or 38% to about 50%, meaning that the length of the portion of stress member 4 disposed within the mounted bladder is, for example, 48% longer than the relaxed length of the hollow portion of the bladder. More preferably, the axial prestress is from about 35% or 36% to about 44% or 45%, and most preferably it will be about 40%. Tests with axial stresses as high as 150% indicate that although performance is acceptable, the unit is difficult to manufacture and the elastic material of the bladder 2 does not favorably respond to storage at such a high stress. In addition, overstressed units tend to walk off of the stress member with time and also the adverse effects of degradation of the material of the bladder 2 are accentuated under a high axial or radial stress. Furthermore, too great an axial and/or radial stress has an adverse impact upon the filling capacity of the bladder 2. Axial prestressing of less than about 10–15% has been determined to be too low to produce the desired output flow rate when only small quantities of liquid remain in the bladder.

The radial prestress of the uninflated bladder is between about 10% and 100%, preferably is between about 15% and 40%, more preferably is between about 18% and 25%, and most preferably is about 20% or 22%. It has been determined that radial prestressing in excess of about 100% and less than about 5–10% present the same difficulties discussed in connection with over and under axial stressing.

Filling the system is advantageously accomplished by a syringe or other delivery apparatus such as a variety of pumps commonly used by pharmacists, sealingly engaged in fluid communication with lumen 13, preferably by means of an appropriate luer for engaging a male luer 17 provided in filling port 11. For example, with a syringe containing the desired pharmaceutically active material in fluid communication with influent lumen 13, the syringe is compressed generating a fluid pressure which pushes aside the valve band 22 thereby allowing fluid to enter the interior 15 of bladder 2 by way of transverse influent duct 14. The bladder 2 may be constructed to hold any desired amount of fluid. In one specific design of an infusion pump embodying the invention which has been constructed and successfully tested, the bladder was designed to hold a maximum volume of about 105 ml. Due to the prestressing of bladder 2, the system is capable of being charged with amounts less than the maximum capacity, and still delivering at the constant predetermined flow rate.

The bladder 2 and stress member 4 are preferably designed such that filling expands the bladder radially, but the axial length of the bladder 2 is essentially unchanged upon filling.

Upon release of pressure from the syringe, the resilient properties of the valve band 22 act in cooperation with fluid pressure generated by the stressed bladder, to close transverse influent duct 14 thereby preventing escape via lumen 13 of the pressurized pharmaceutically active material contained in the interior 15 of the bladder 2. The fluid pressure within the fully extended bladder will likely be in the area of about 8–10 psi. Any air that may be trapped within effluent duct 24 or effluent lumen 25 may be expelled by way of tubing 31 and the effluent flow may then be stopped by means of a conventional tubing clamp 39 on tubing 31. The clamp 39 on effluent tubing 31 will normally be clamped before catheterization.

Upon release of a clamp on the tubing 31, the fluid pressure in the bladder will cause a known flow to occur through the capillary tube 28.

Due to the axial prestressing of bladder 2, a pressure profile generated by deflation of the bladder 2 will be substantially constant over the delivery volume. The radial prestress on the bladder 2 assures that the initial entry of the first 1–2 ml of fluid will immediately create maximum pressure to occur in the bladder 2 since essentially no fluid is necessary to bring the material of the bladder to its elastic limit. An additional function of the prestressing of the bladder 2 is to ensure that the bladder is empty before it is filled with liquid, i.e., that no air will be disposed between the deflated bladder 2 and the adjacent exterior wall of internal stress member 4. The only air in the system will be that contained in the lumen 13 and 25 and I.V. line 31, which can be expelled after filling the bladder and prior to catheterization. Thus, the likelihood of air being available for delivery to a patient is minimized and only a minimal amount of the pharmaceutically active material will remain in the unit after infusion due to compression of the bladder 2 radially inwardly against stress member 4.

While the infusion pump of the present invention is in operation, the amount of pharmaceutically active material remaining in the bladder 2 at any time may, of course, be qualitatively evaluated by observing the size of the bladder 2 through the transparent material of outer casing 3. However, a more quantitative estimation of remaining service time is obtained by providing the internal stress member with a series of small indicator bumps 16 or raised areas along the surface thereof, which will only be visible when the bladder 2 shrinks back onto the stress member 4 in close conformity to the surface thereof. This plurality of raised indicator bumps 16 may be, for example, disposed in a colinear arrangement along the axial direction of the internal stress member 4, and spaced apart such that the sequential appearance of each bump during deflation of bladder 2 may be correlated with a particular volume of remaining pharmaceutical material in the bladder 2. Also, due to the predictability of the rate of discharge as a function of the diameter and length of a capillary tube 28, it is possible to correlate the appearance of each of a series of raised indicators on the internal stress member with a particular time remaining between the time the indicator means becomes visible and the time that the pharmaceutical material has been completely expelled.

Although this invention has been described in terms of certain preferred embodiments, other embodiments that are apparent to those of ordinary skill in the art are also within the scope of this invention. Accordingly, the scope of the invention is intended to be defined only by reference to the appended claims.

What is claimed is:

1. An infusion pump for delivering a quantity of fluid material at a substantially constant flow rate, comprising:

an elongate elastomeric bladder having a central lumen and at least one open end;

an elongate stress member means of substantially constant diameter extending continuously throughout and along the length of and within the lumen of the bladder, and having a fluid-tight seal to the bladder;

a filling port in the stress member means in communication with the lumen of the bladder through a first lumen extending through the stress member means; and an exit port in the stress member means in communication with the lumen of the bladder through a second lumen extending through the stress member, the stress member means acting to minimize pressure surging at the terminal end of the deflation cycle, by having a diameter that is from 1.1 to 2.0 times the unstressed internal diameter of the bladder, an axial length of the bladder at the fluid-tight seal which is substantially unchanged upon filling the fluid material.

2. An infusion pump for delivering a quantity of fluid material at a substantially constant flow rate, comprising:

an elongate elastomeric bladder having a central lumen and at least one open end;

an elongate stress member extending of substantially constant diameter continuously throughout and along the length of and within the lumen of the bladder, and having a fluid-tight seal with the bladder, and acting to provide a substantially constant fluid pressure within said bladder; and at least one flow path in the stress member in fluid communication with the central lumen of the bladder, said stress member having a diameter that is from 1.1 to 2.0 times the internal relaxed diameter of the bladder, and the length of the stress member is from 1.1 to 2.5 times the internal relaxed length of the bladder, and the axial length of the bladder at the fluid-tight seal is substantially unchanged upon filling the fluid material.

3. An infusion pump as in claim 2, further comprising a flow regulator in the flow path.

4. An infusion pump for delivering a quantity of fluid material at a substantially constant flow rate, comprising:

an elongate elastomeric bladder having a central lumen and at least one open end;

an elongate stress member extending throughout the length of and within the lumen of the bladder and having a fluid-tight seal to the bladder;

a filling port on the stress member in communication with the lumen of the bladder by way of a first lumen extending through the stress member;

an exit port on the stress member in communication with the lumen of the bladder by way of a second lumen extending through the stress member and non-intersecting the first lumen; and a flow regulating means disposed upstream of the exit port wherein the stress member prestresses the bladder in both the axial and radial directions prior to introduction into the bladder of any of the fluid material, and the axial length of the bladder is essentially unchanged upon filling with the fluid material.

5. An infusion pump for delivering a quantity of fluid material at a substantially constant flow rate as in claim 4, wherein the radial prestressing is within the range of from about 10% to about 100%.

* * * * *